United States Patent [19]

Pasero et al.

[11] Patent Number: 5,348,862
[45] Date of Patent: Sep. 20, 1994

[54] METHOD FOR THE RAPID DETERMINATION OF THE MICROORGANISM CONTENT OF LIQUIDS AND FLUID SOLUTIONS, AND APPARATUS FOR IMPLEMENTING THIS METHOD

[75] Inventors: Edoardo Pasero, Genoa; Carlo Rossetti; Franco Aiolfi, both of Milan, all of Italy

[73] Assignee: Biosensori S.p.A., Italy

[21] Appl. No.: 947,477

[22] Filed: Sep. 21, 1992

[30] Foreign Application Priority Data

Nov. 20, 1991 [IT] Italy .................... 91 A 000150

[51] Int. Cl.⁵ .................... C12Q 1/06; G01N 21/00
[52] U.S. Cl. .................... 435/39; 435/291; 435/294; 435/311; 435/817; 204/403; 204/415; 204/416; 204/435; 422/68.1; 422/82.01; 422/82.02; 422/82.03; 422/102; 436/63; 436/150; 436/806
[58] Field of Search ........... 435/39, 291, 294, 311, 435/817; 204/403, 415, 416, 435; 422/68.1, 82.01, 82.02, 82.03, 102; 436/63, 150, 806

[56] References Cited

U.S. PATENT DOCUMENTS

| 4,246,343 | 1/1981 | Wilkins et al. | 435/39 |
| 4,264,728 | 4/1981 | Wilkins | 435/291 |
| 4,517,291 | 5/1985 | Seago | 435/291 |
| 4,614,716 | 9/1986 | Rohrback et al. | 435/39 |
| 5,126,034 | 6/1992 | Carter et al. | 204/403 |

FOREIGN PATENT DOCUMENTS

| 219247 | 4/1987 | European Pat. Off. | G01N 27/30 |
| 221663 | 5/1987 | European Pat. Off. | C12Q 1/02 |
| 238322 | 9/1987 | European Pat. Off. | C12Q 1/02 |
| 352138 | 4/1990 | European Pat. Off. | G01N 27/26 |

OTHER PUBLICATIONS

Food Microbiology vol. 6, No. 3, 1989, USA, pp. 159-169 R. A. Patchett et al.: Rapid detection of bacteria . . . .
Journal of Applied Bacteriology, vol. 66, No. 1, 1989, UK pp. 49-55: R. A. Patchet et al.: Investigation of a simple . . . .

*Primary Examiner*—Michael G. Wityshyn
*Assistant Examiner*—Abdel A. Mohamed
*Attorney, Agent, or Firm*—Larson and Taylor

[57] ABSTRACT

Method for amperiometrically measuring the bacterial content of liquids in a bioelectrochemical cell wherein the mediator is initially oxidized in the cell, then brought into contact with a capturing system containing the bacteria of the sample, resulting in a first response at the electrodes, and finally brought into contact again with the capturing system after the bacteria present have been killed, producing a second response due to the interfering substances, which is subtracted from the first response. An apparatus is also provided for implementing this method.

8 Claims, 2 Drawing Sheets

METHOD FOR THE RAPID DETERMINATION OF THE MICROORGANISM CONTENT OF LIQUIDS AND FLUID SOLUTIONS, AND APPARATUS FOR IMPLEMENTING THIS METHOD

The present invention concerns the rapid determination of the bacterial activity in a fluid sample using a bioelectrochemical cell. More specifically it relates to a method for effecting such a determination whereby a considerable increase in the bacterial response can be obtained, eliminating any interference caused by the base current and/or by substances which could interact with the determination itself.

Determination of the bacterial content of liquids and fluid solutions is of particular importance in a wide variety of sectors, such as the food industry, monitoring of environmental pollution, monitoring of industrial effluent, clinical analysis and medical diagnosis in general.

The standard methods currently used for determining the bacterial content of liquids consist in the culture of the sample under given environmental conditions and in appropriate culture media, and in the subsequent counting of the bacterial colonies; the major drawbacks of these methods lie in the duration of the analysis, since at least 18 hours are required to achieve the formation of visible colonies, and in the need for individual counting of the colonies.

The methods recently proposed include alternative analytical methods of the bioelectrochemical type, based on the direct measurement of the metabolic activity of the bacteria present in the sample, carried out amperometrically in bioelectrochemical cells using suitable mediators.

The use of bioelectrochemical cells for the rapid determination of the bacterial content has been investigated by numerous researchers over the past few years. For example, reference is made to the research work described in Appl. Microbiol. Biotechnol. (1988) 28, 26 and J. Appl. Bacteriol. (1989) 66, 49.

Further aspects of the bioelectrochemical detection systems are described in European Patent Applications No. 221,663 (Method and instrument for measuring the microbic activity in a bioelectrochemical cell); No. 219,247 (Bioelectrochemical cell and associated electrode); No. 238,322 (Mediators for bioelectrochemical cells); No. 352,138 (Bioelectrochemical electrodes). In some of the systems described, the bacteria are concentrated on a filter before the analysis is performed, other systems involve special configurations of the cell electrodes, while yet other systems involve specific compositions of the mediators used to convey the electrons to the measuring electrode.

All these known systems, however, have the drawback that the measurements obtained with them may be influenced by the state of oxidation of the mediator, by base currents, as well as by interference with substances which are able to release electrons to the mediator and which may be present in the sample being examined and/or in the filter.

The main object of the present invention, therefore, is to provide a system for determining the bacterial content using amperometric means in a bioelectrochemical cell, which is able to overcome the drawbacks and disadvantages of the systems of the known art.

According to a main characteristic feature of the present invention, the electron transfer mediator in a bioelectrochemical cell, dissolved in suitable saline solutions containing all the necessary ions for promoting the vitality and growth of the bacteria, is first oxidised by recirculating it inside the measuring cell to whose electrodes a suitable potential difference is applied. After the mediator, in contact with the working electrode, has been oxidised completely and the corresponding current between the electrodes has fallen to a constant level, a filter, on which the bacteria contained in the sample have previously been captured, is inserted in the circuit; the response generated by the contact between the mediator and the bacteria is detected at the electrodes and recorded; at this point, the filter is again excluded from the circuit and washed with a strong biocide; after the bacteria have been killed, the filter is inserted again into the mediator circuit, resulting in a new response dependent upon the contact between the mediator and any interfering substances previously present on the filter together with the bacteria (including the materials which make up the filter itself). The measurement provided by the instrument is constituted by the difference between the two abovementioned responses.

In this way, the measurement relates solely to the bacterial content present, following elimination of any interference with possible additional currents dependent upon the state of oxidation of the mediator and following subsequent elimination of all possible interference with substances which are able to release electrons to the mediator and which may be present in the sample or in the filter.

By limiting and keeping the base current constant, the selectivity and level of response can be increased considerably, as will appear more clearly from the examples of application described below.

Stabilisation of the base current at a very low and constant value, after the mediator has been oxidised, is achieved, moreover, by applying a suitable cut-off membrane as a protection for the reference electrode so as to allow the passage of the current conveyed by small ions, while preventing at the same time direct contact between this electrode and the mediator and hence reduction of the latter by the electrode in question.

BRIEF DESCRIPTION OF THE DRAWINGS

Further objects and advantages of the present invention will emerge more clearly during the course of the following detailed description of the same, with reference to the accompanying drawings, in which.

Figure 1:
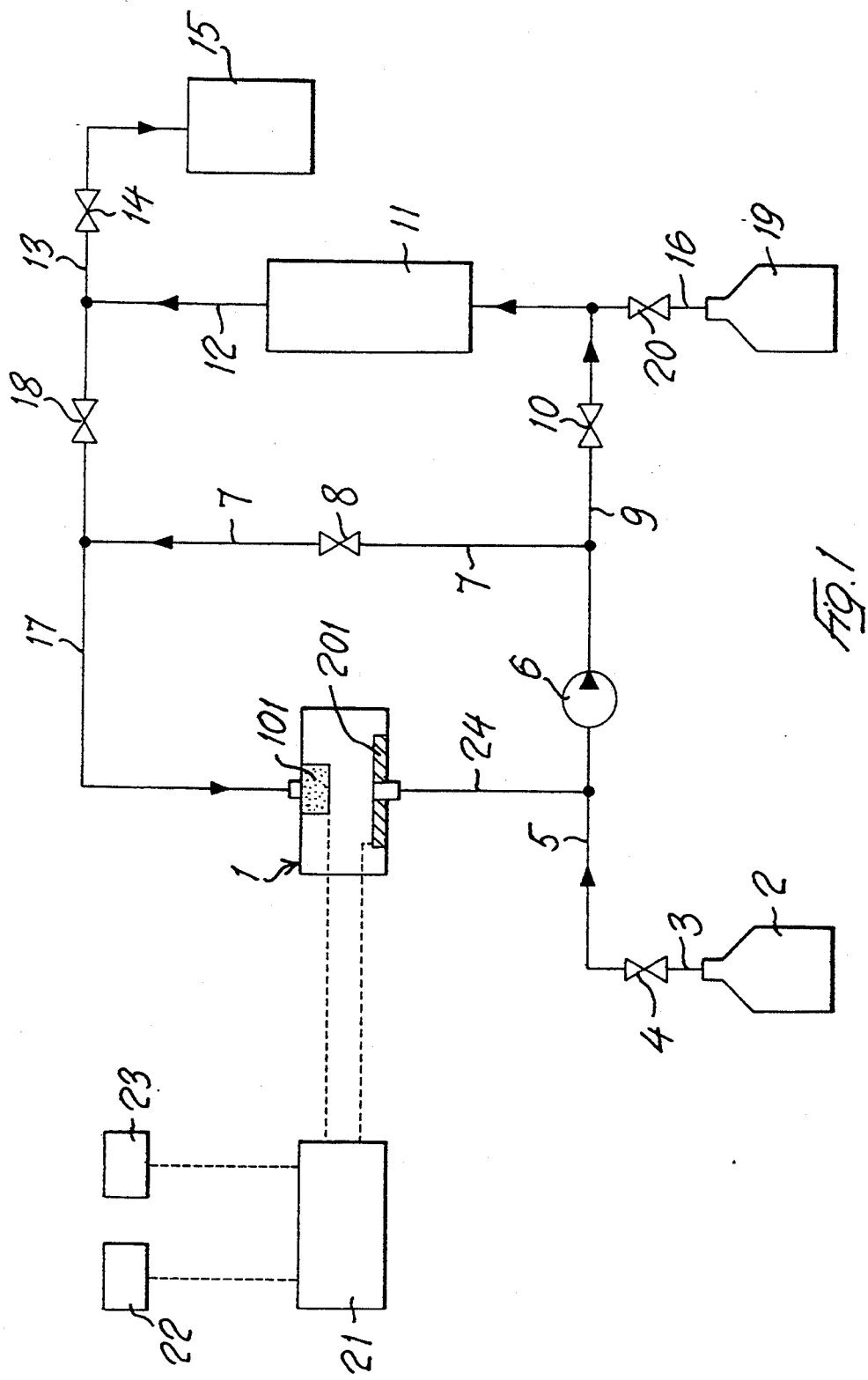
FIG. 1 is a diagram of a system for implementing the method according to the invention.

With reference to the drawings and with particular reference to FIG. 1 thereof, the system for determining the bacterial content of a fluid solution according to the present invention comprises a bioelectrochemical cell 1 which accommodates, in a manner known per se, the electrodes between which the solution to be analysed, containing the mediator, is made to circulate, more specifically the working electrode 101, consisting preferably of a porous disc which is made of sintered graphite or other current-conducting material and is preferably pervious to the abovementioned solution, and the reference electrode 201, typically consisting of silver and silver chloride, which for example can be imprinted by means of serigraphy on the bottom of the cell. This electrode is advantageously covered by a special membrane (cut-off membrane, not shown) pervious to the small ions but not to the mediators used in the test.

2 denotes the container holding the mediator. The so-called "mediators" preferably consist of substances with relatively low redox potentials, which accept electrons from the microorganisms, have a reversible electrochemistry, are chemically stable, are non-auto-oxidisable and are normally soluble in aqueous solutions. Typical mediator agents used for implementing the method according to the present invention are sodium or potassium ferrocyanide, or benzoquinone, or mixtures thereof.

The container 2 communicates, via the tube 3 and the shut-off solenoid valve 4, with the tube 5 connected to the suction side of a peristaltic pump 6. The delivery side of the pump 6 communicates with a branched line 7, provided with a shut-off solenoid valve 8, and with a circulating line 9, provided with a shut-off solenoid valve 10, which in turn communicates with the inlet side of an absolute filter 11 for retaining and concentrating the bacteria contained in the sample. The filter 11, which must be replaced after each test has been performed, contains a filtering element for total bacterial retention, which element may be preceded by a pre-filter in the case where samples to be analysed cannot be conveyed directly to an absolute filter.

The outlet of the filter 11 is connected to a tube 12 which communicates on one side with the tube 13 connected, via a shut-off solenoid valve 14, with a discharge vessel 15. On the other side, the tube 12 communicates with a tube 17, via the shut-off solenoid valve 18. The tube 17 communicates in turn with the inlet of the cell 1. The outlet of the cell 1 communicates, via the tube 24, with the suction side of the pump 6.

19 denotes a container for a biocidal liquid, intended for the purposes described in more detail below. It is possible to use as a biocidal substance any substance designed to kill the bacterial strains being analysed, for example sodium hypochlorite, formaldehyde and chlorine dioxide.

The container 19 is connected, via the tube 16 and the shut-off solenoid valve 20, to the inlet side of the absolute filter 11.

21 denotes an electronic circuit for processing the data from the electrodes 101 and 201, while 22 denotes a display for reading-off the results, and 23 a printer, both associated with the processing circuit 21.

When implementing the method according to the invention, the solution containing the mediator, the nutritional substrate and a suitable buffer are introduced into the container 2. Then, the valves 10 and 18 of the flow circuit of the apparatus are closed, while simultaneously opening the valve 8 of the branched circuit 7 and the valve 4 associated with the container 2, and the pump 6 is activated. In this way, the solution comprising the mediator is introduced into the circuit consisting of the tube 5, pump 6, tube 7, solenoid valve 8, tube 17, cell 1 and tube 24 and recirculated there until the circulating mediator has been completely oxidised. At the same time, a suitable quantity of the sample to be analysed is filtered through the absolute filter 11, which retains inside it the entire bacterial population present.

At the end of filtering, the filter 11 is washed with a suitable solution, for example an aqueous solution of $Na_2HPO_4$ 40 mM; $NaH_2PO_4$ 20 mM; $(NH_4)_2SO_4$ 7.6 mM and NaCl 20 mM (pM =6.5) and then inserted into the mediator flow circuit by opening the solenoid valves 10 and 18 and closing the solenoid valve 8. During this phase, the solenoid valves 14 and 20 are also closed. During this phase, the mediator therefore flows from the pump 6 to the tube 9 and via the solenoid valve 10 into the absolute filter 11, and from the latter through the tube 12, the solenoid valve 18 and the tube 17 into the cell 1 where it passes through the porous electrode 101 and reaches the outlet 24, after passing over the reference electrode 201. In this way, it is possible to avoid contamination of the cell by the bacteria since the mediator, after coming into close contact with the latter, undergoes filtration as it passes through the absolute filter before returning to the cell. Within a few seconds following insertion of the filter, the instrument's response is detected at the electrodes 101, 201 and recorded. The filter is then excluded from the circuit by closing the valves 10 and 18 and, after opening the valves 20 and 14, is passed through by the biocidal solution contained in the storage vessel 19, which is then discharged into the storage vessel 15. Subsequently, the valves 14 and 20 are closed, and the flow circuit is restored by opening the valves 10 and 18, thus producing a new response at the electrodes. The difference between the two abovementioned responses is automatically converted by the instrument into the measurement of the bacterial content.

Figure 2:
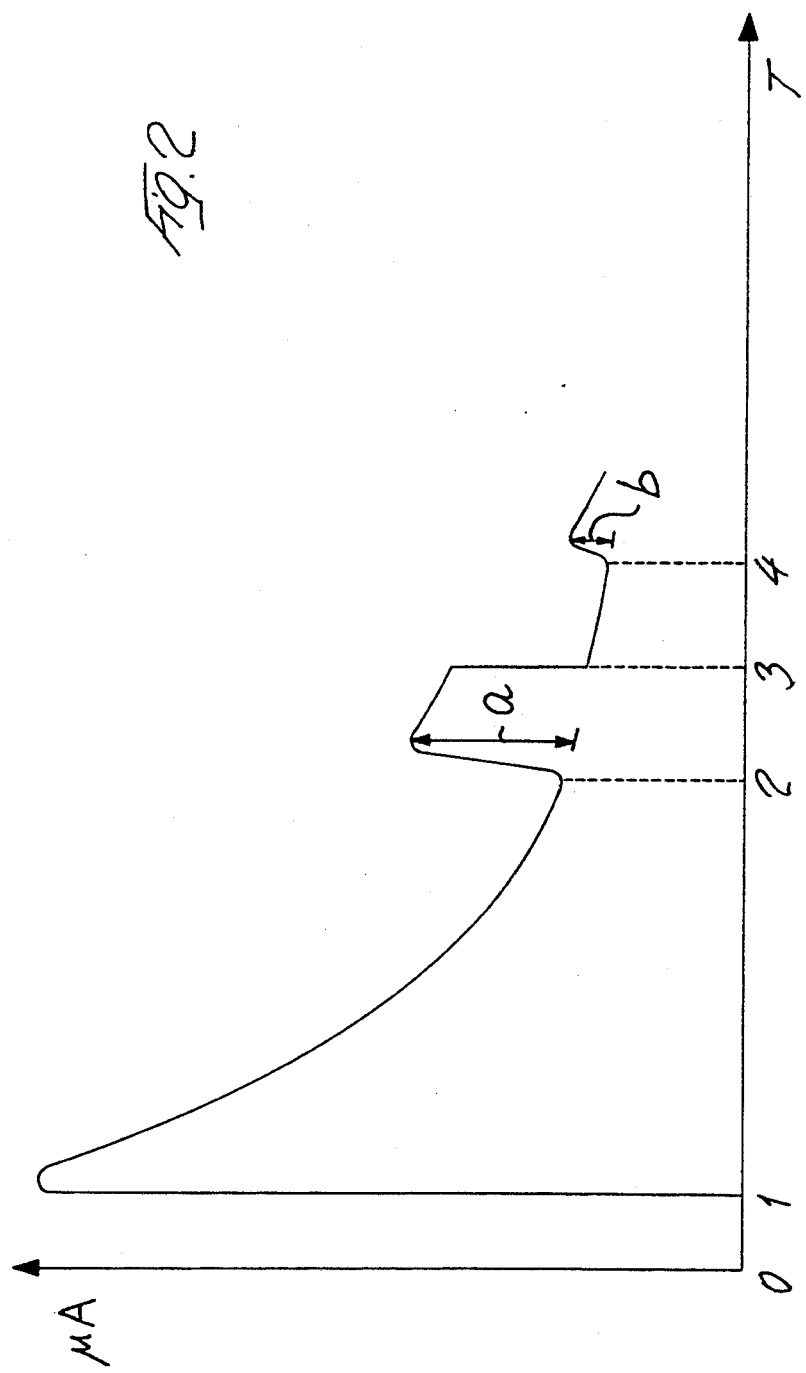
FIG. 2 is a diagram illustrating the signal detected at the measuring electrodes of the system according to FIG. 1.

FIG. 2 shows a diagram whose abscissae represent the times and ordinates the current at the electrodes 101, 102 expressed in $\mu A$. The first section of the diagram, from the time 1 to the time 2, represents the settling phase for oxidation of the mediator liquid. The section (a) from the time 2 to the time 3 represents the first response parameter at the electrodes, after insertion of the filter with the live bacteria. From the time 3 to the time 4 washing with the biocide is performed, and at the time 4 the washed filter is inserted. (b) represents the response parameter, at the electrodes, of the reducing substances not due to the live bacteria and present on the filter. The difference (a−b) represents the response of the bacterial content of the sample. This difference is suitably processed at 21 and then displayed at 22 and 23 in the customary manner.

Some of the responses obtained using the device described above are given below for individual bacteria strains diluted to varying concentrations in a suitable medium; the responses obtained by the instrument are shown in the following table, with respect to the total quantity of bacteria on the filter (determined using the traditional plate-count method:

TABLE

| BACTERIAL STRAIN | BACTERIA ON THE FILTER (UFC) | RESPONSE ($\mu A$) |
|---|---|---|
| Pseudomonas fluorescens | $1.2 \times 10^6$ | 1.5 |
| | $7.5 \times 10^6$ | 10 |
| | $1.5 \times 10^7$ | 21 |
| | $2.3 \times 10^7$ | 28 |
| Escherichia coli | $3.6 \times 10^6$ | 3 |
| | $2.5 \times 10^7$ | 29 |
| | $5 \times 10^7$ | 60 |
| | $7.2 \times 10^7$ | 76 |
| Enterobacter cloacae | $1.5 \times 10^6$ | 2 |
| | $3 \times 10^6$ | 4 |
| | $1 \times 10^7$ | 13 |
| | $5 \times 10^7$ | 74 |
| Serratia marcescens | $6 \times 10^5$ | 0.5 |
| | $3 \times 10^6$ | 8 |
| | $6 \times 10^6$ | 15 |
| | $1.8 \times 10^7$ | 45 |
| Lactobacillus bulgaricus | $2.1 \times 10^5$ | 0.5 |
| | $1 \times 10^6$ | 4.5 |

TABLE-continued

| BACTERIAL STRAIN | BACTERIA ON THE FILTER (UFC) | RESPONSE ($\mu A$) |
|---|---|---|
| | $2.1 \times 10^6$ | 10 |
| | $8.4 \times 10^6$ | 34 |

In an alternative version of the present invention, after filtration of the sample, the filter is subjected to incubation under suitable culture conditions and for a given period of time and subsequently inserted in the circuit so that measurement can be effected. This enables the sensitivity of the instrument to be increased substantially and furthermore, by adopting specific culture environments and media, the said instrument can be made selective for given bacterial strains.

Obviously, the present invention is not limited to the embodiments described and illustrated, but comprises all those variants and modifications which fall within the widest scope of the inventive idea, substantially as claimed below.

We claim:

1. Method for measuring the bacterial content of liquids using amperometric means in a bioelectrochemical cell comprising initially oxidizing an electron transfer mediator in the cell, then bringing the mediator into contact with a filter containing the bacteria of a liquid sample, to produce a first response at the electrodes, and finally bringing the mediator into contact again with the filter after the bacteria present have been killed by chemical means to produce a second response due to interfering substances, which is subtracted from the first response to produce data representative of the bacterial content of the sample.

2. Method according to claim 1, wherein the mediator is dissolved in a saline solution containing all the necessary ions for keeping the bacteria alive.

3. Method according to claim 1 the reference electrode of the bioelectrochemical cell is protected with a membrane pervious to small ions, but impervious to mediators used for the amperometric detection of the metabolic activity of bacteria.

4. Method according to claim 1 wherein the working electrode of the bioelectrochemical cell consists of sintered graphite or of any other porous current-conducting material.

5. Method according to claim 1 in which the sample to be analysed is filtered using filter which is subsequently washed and inserted in the measuring circuit after the mediator has been oxidised.

6. Method according to claim 1, wherein the bacteria retained on the filter are subjected to incubation before insertion of the filter in the measuring circuit.

7. Method for measuring the bacterial content of liquids using amperometric means in a bioelectrochemical cell according to claim 1 comprising the introduction of a solution containing the mediator into the cell circuit; circulation of the solution until the mediator has been completely oxidised; filtration of the sample via the filter; washing of the filter; insertion of the filter into the cell circuit; detection of a first amperometric response; further washing of the filter with a biocide; insertion of the filter into the circuit again; detection of a second amperometric response which is subtracted from the first response; and conversion of the resultant datum into the measurement of the bacterial content.

8. Device for implementing the method according to claim 1 comprising a bioelectrochemical cell; a first flow circuit which connects an outlet of the cell to an inlet of the cell; means for circulating a mediator liquid in this circuit; a second flow circuit in parallel with said first flow circuit which connects the outlet of the cell to the inlet of filter, and the outlet from this filter to the inlet of the cell; valve means for alternately bringing into circulation said first or said second flow circuit; a storage vessel for a mediator liquid designed to communicate with said first flow circuit so as to supply said first flow circuit with a quantity of mediator solution; a storage vessel for a biocidal liquid designed to communicate with said filter so as to cause a biocidal liquid to circulate therein; and a data processing circuit connected to the output of the electrodes of the bioelectrochemical cell for processing the amperometric data supplied by said electrodes.

* * * * *